United States Patent
Konaka et al.

(10) Patent No.: US 8,156,794 B2
(45) Date of Patent: Apr. 17, 2012

(54) INDENTING TYPE MATERIAL TESTING MACHINE, TESTING METHOD, AND TESTING PROGRAM PRODUCT

(75) Inventors: Yasunori Konaka, Kyoto (JP); Toyokazu Maeda, Nagaokakyo (JP)

(73) Assignee: Shimadzu Corporation, Kyoto-shi (JP)

( * ) Notice: Subject to any disclaimer, the term of this patent is extended or adjusted under 35 U.S.C. 154(b) by 480 days.

(21) Appl. No.: 12/305,280

(22) PCT Filed: Jun. 20, 2006

(86) PCT No.: PCT/JP2006/312294
§ 371 (c)(1),
(2), (4) Date: Dec. 17, 2008

(87) PCT Pub. No.: WO2007/148380
PCT Pub. Date: Dec. 27, 2007

(65) Prior Publication Data
US 2010/0229637 A1    Sep. 16, 2010

(51) Int. Cl.
*G01N 3/48* (2006.01)
*H03F 1/26* (2006.01)
*H04B 15/00* (2006.01)
*G06F 17/10* (2006.01)

(52) U.S. Cl. ............... 73/81; 708/300; 702/191
(58) Field of Classification Search .......... 327/551, 327/557; 73/81–83
See application file for complete search history.

(56) References Cited

U.S. PATENT DOCUMENTS
2003/0080721 A1  5/2003  Lee
2003/0215100 A1* 11/2003  Kimura et al. ............... 381/71.1
2005/0204820 A1*  9/2005  Treiber et al. ................ 73/649

FOREIGN PATENT DOCUMENTS

| | | |
|---|---|---|
| DE | 19983795 T1 | 1/2002 |
| JP | 5-85019 A | 4/1993 |
| JP | 7-55482 A | 3/1995 |
| JP | 7-55482 Y2 | 12/1995 |
| JP | 2001-296225 A | 10/2001 |
| JP | 2001296225 A * | 10/2001 |
| JP | 2003-279458 A | 10/2003 |
| JP | 2003-337094 A | 11/2003 |
| JP | 2004-537051 A | 12/2004 |
| JP | 2005-331256 A | 12/2005 |
| WO | 00/34744 A1 | 6/2000 |

OTHER PUBLICATIONS

NPL, Machine Translation of Application Publication, JP2001296225, Translated on: Feb. 16, 2011, By: AIPN-Advanced Industrial Property Network, National Center for Industrial Property Information and Tranining, Japan Patent Office.*
Germany Office Action dated Jun. 16, 2010, issued in corresponding Germany Patent Application No. 112006003935.0-53.
International Search Report of PCT/JP2006/312294, date of mailing Sep. 12, 2006.

* cited by examiner

*Primary Examiner* — Lisa Caputo
*Assistant Examiner* — Roger Hernandez-Prewitt
(74) *Attorney, Agent, or Firm* — Westerman, Hattori, Daniels & Adrian, LLP

(57) ABSTRACT

An indenter is pressed onto a test piece; a displacement of the indenter is detected; and a testing force applied to the test piece through the indenter is detected. FFT analysis is performed on a displacement detection signal detected in a non-load state to detect a frequency band of noise. Filter characteristics are calculated based on the detected frequency band, and filtering is performed on the displacement detection signal based on the filter characteristics. Physical properties of the test piece are evaluated based upon the displacement detection signal after the filtering and the testing force.

9 Claims, 6 Drawing Sheets

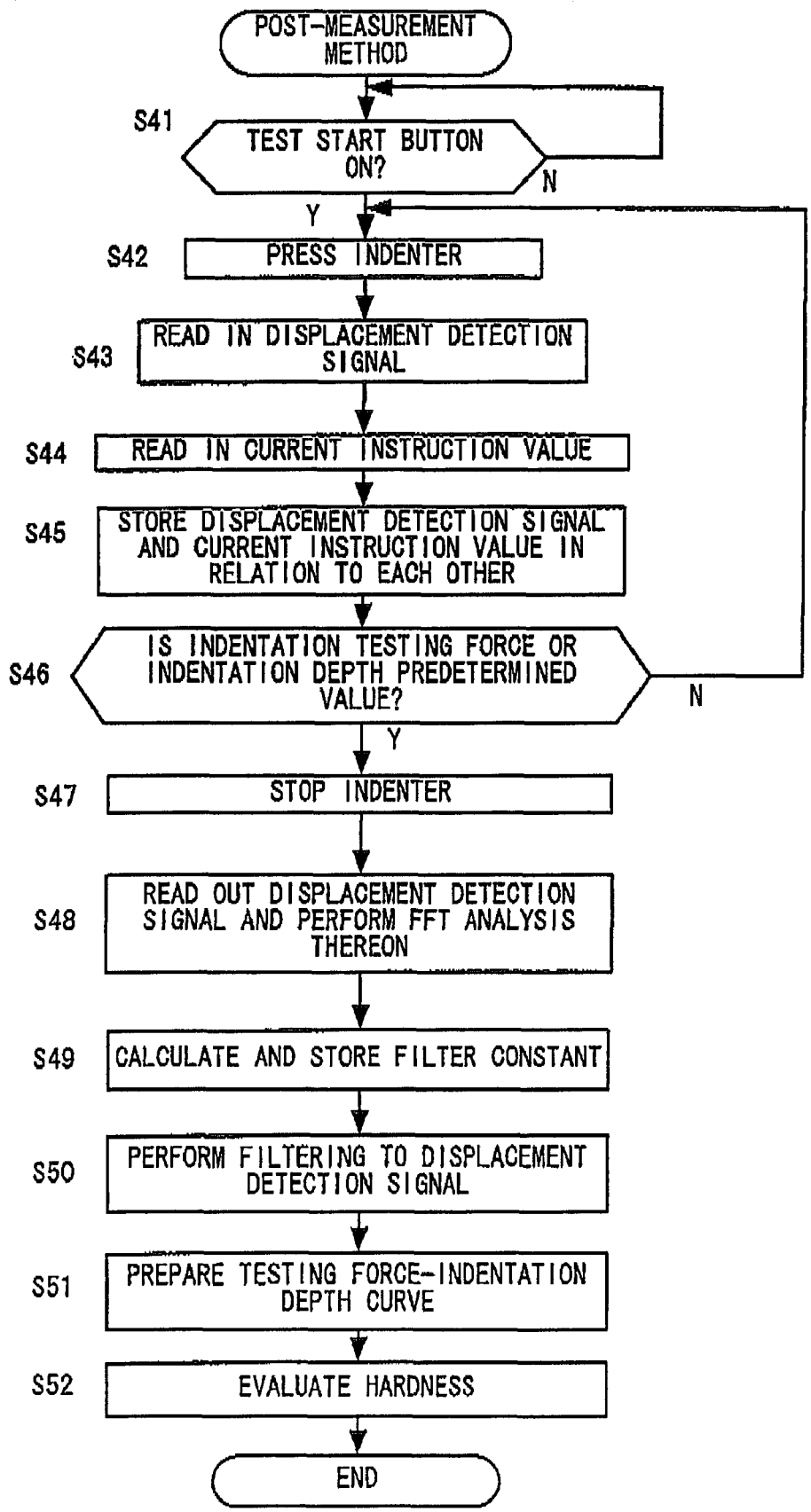

INDENTING TYPE MATERIAL TESTING MACHINE, TESTING METHOD, AND TESTING PROGRAM PRODUCT

TECHNICAL FIELD

The present invention relates to an indenting type material testing machine, a testing method, and a testing program product in which an indenter, etc., is pressed onto a test piece by a minute load and evaluates the material.

BACKGROUND ART

Patent Document 1 discloses a micro hardness meter that presses an indenter onto a test piece, detects the displacement of the indenter in response to its press load, and measures the hardness of the test piece. In this kind of micro hardness meter, the press load at which the indenter is pressed onto a test piece is very minute and the measurement result could be adversely affected, since the hardness meter itself might vibrate due to noise and vibration of surroundings.

On the other hand, Patent Document 2 discloses a testing machine that includes a preliminarily selected filter interposed in a circuit for extracting detection output of the test force applied to a test piece or elongation of the test piece in order to remove noises in the detection signal. In this testing machine, the noise removal of the detection output is done by using a filter characteristic selected from among a plurality of filter characteristics set beforehand.

[Patent Document 1] Japanese Laid-Open Application No. 05-85019.

[Patent Document 2] Japanese Patent Laid-Open Application No. 2005-331256

SUMMARY OF THE INVENTION

Problem to be Solved by the Invention

In a testing machine like the micro hardness meter that is portable, turbulence is different in each host site. Therefore, if no filter characteristic that is appropriate for the turbulence of the host site exists in the plurality of filter characteristics described in Patent Document 2, the turbulence could not be removed appropriately.

Means for Solving the Problem (1) An indenting type material testing machine according to the present invention includes: an indenter pressed onto a test piece; a load device that applies a load to the test piece through the indenter; a displacement sensor that measures displacement of the indenter; a calculation device that calculates filter characteristics that remove a turbulence component in a displacement detection signal based on the displacement detection signal obtained from the displacement sensor in a no-load state; a storage unit that stores the filter characteristics calculated by the calculation device; and a filtering device that performs filtering to the displacement detection signal based on the filter characteristics stored in the storage device.

(2) The indenting type material testing machine may further include: a selection member that selects any one of a preparation mode in which the displacement signal is sampled to calculate the filter characteristics and a test mode in which the displacement detection signal is sampled to calculate material evaluation data. In this case, when the preparation mode is selected, the displacement detection signal is sampled, with the indenter being held in a position in a no-load state.

(3) An indenting type material testing machine according to another aspect of the invention includes: an indenter pressed onto a test piece; a load device that applies a load to the test piece through the indenter; a displacement sensor that measures displacement of the indenter; a calculation device that calculates filter characteristics that remove a turbulence component in a displacement detection signal based on the displacement detection signal obtained from the displacement sensor in a loaded state; a storage unit that stores the filter characteristics calculated by the calculation device; and a filtering device that performs filtering to the displacement detection signal based on the filter characteristics stored in the storage device.

(4) The calculation device of the material testing machine can calculate the filter characteristics based on the displacement detection signal sampled in an initial stage of starting pressing of the indenter. In this case, the filtering device can perform the filtering process to the displacement detection signal output thereafter according to the filter characteristics.

(5) The indenting type material testing machine described above can further include: an arithmetic device that calculates an indentation depth of the indenter-testing force curve based on the detection signal from the displacement sensor having subjected to the filtering process by the filtering device and an indenting force of the indenter by the load device to calculate the hardness of the test piece.

(6) A testing method according to the present invention includes: pressing an indenter onto a test piece; detecting displacement of the indenter; detecting a testing force applied to the test piece by the indenter; detecting a frequency band of noise in the detected displacement detection signal of the indenter; calculating filter characteristics based on the detected frequency band; filtering the displacement detection signal based on the calculated filter characteristics; and evaluating physical properties of the test piece based on the displacement detection signal after the filtering and the testing force.

(7) In the testing method, the displacement detection signal when the frequency band of the noise is detected can be a signal sampled in a no-load state in which the indenter is not in contact with the test piece. Furthermore, in the testing method, the displacement detection signal when the frequency band of the noise is detected can be a signal sampled in a loaded state in which the indenter presses the test piece.

(8) A program product for testing according to the present invention causing a computer to execute: a process to press an indenter onto a test piece; a process to detect displacement of the indenter; a process to detect a testing force applied to the test piece by the indenter; a process to detect frequency band of a noise to a detected displacement detection signal of the indenter; a process to calculate filter characteristics based on the detected frequency band; a process to perform filtering to the displacement detected signal with the calculated filter characteristics; and a process to evaluate physical properties of the test piece based on the displacement detection signal after the filtering and the testing force.

(9) A material testing machine according to the present invention includes: a measurement device that measures frequency characteristics of a turbulence noise superimposed on a detection signal; an arithmetic device that analyses the frequency characteristics to determine a filter constant; a filtering device that performs filtering defined by the filter constant; and an evaluation device that evaluates a material by using the detection signal subjected to the filtering by the filtering device.

Advantageous Effect of the Invention

According to the present invention, the detection signal can be acquired by calculating a filter characteristic that appropriately removes turbulence due to the vibration, etc. of the host site of the testing machine.

BRIEF DESCRIPTION OF THE DRAWINGS

FIG. 3 is a flowchart that illustrates a program that starts up when power is turned on;

FIG. 6 is a flowchart that, illustrates a test process according to a filter characteristics post-measurement method.

EXPLANATION OF SYMBOLS

4: Indenter
5: Load device
20: Control device
21: CPU

BEST MODE FOR CARRYING OUT THE INVENTION

Figure 1:
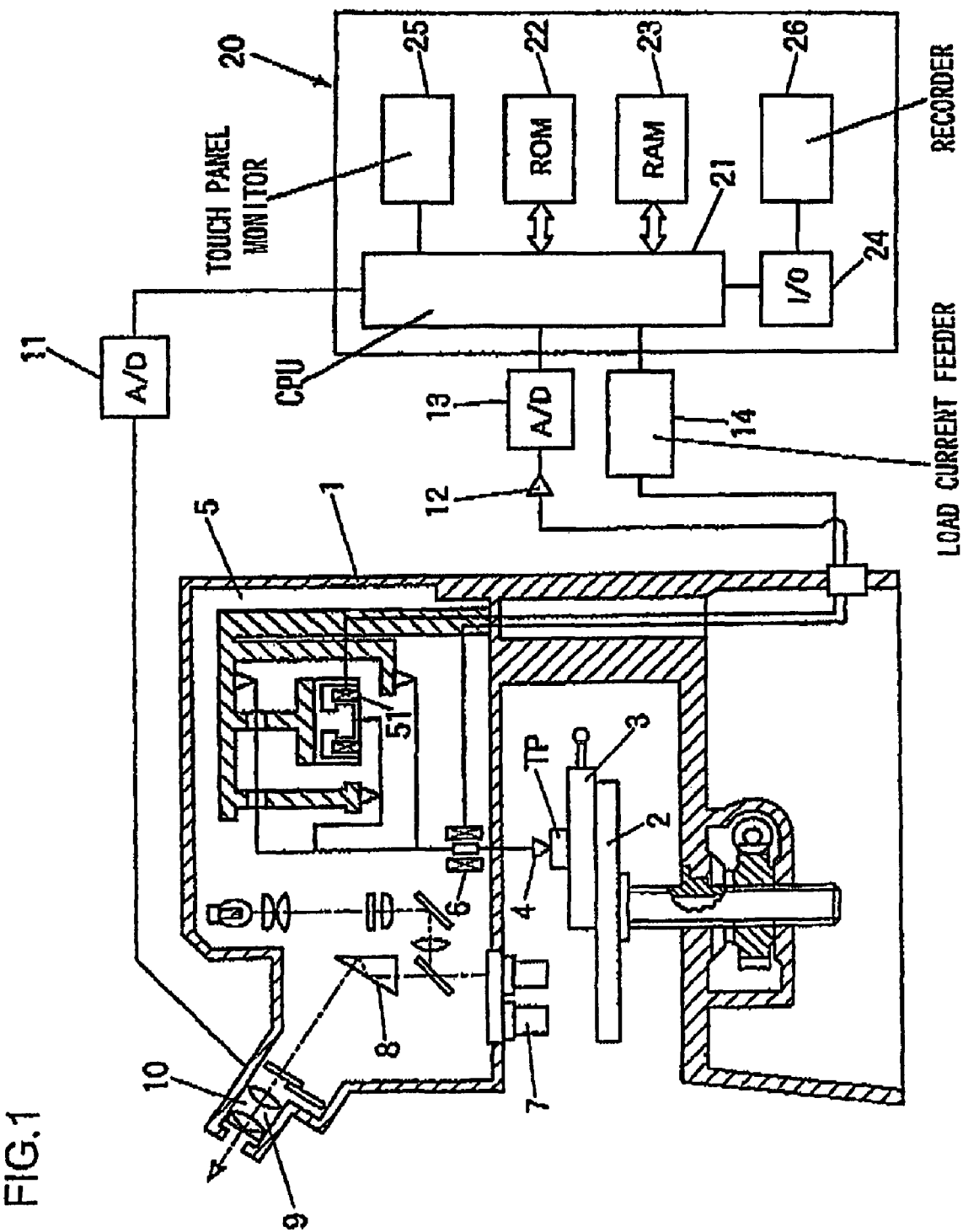
FIG. 1 is a schematic configuration diagram showing an indenting type material testing machine according to an embodiment of the present invention.

FIG. 1 shows one embodiment of the indenting type material testing machine according to the present invention when it is applied to a micro hardness meter. The micro hardness meter of this embodiment includes a function to measure the frequency characteristics of turbulence in the host site, a function to analyze the frequency characteristics of turbulence noises and determine a filter constant, and a function to give a filtering process provided for by the filter constant on the displacement detection output and control the influence of turbulence.

The micro hardness meter includes a frame 1, a table 2 for mounting a test piece disposed to the frame 1 such that it is vertically movable, and a stage 3 that is set on the table 2 and movable in mutually orthogonal X-Y directions. A test piece TP held on the stage 3 is pressed by an indenter 4. In the frame 1, there are housed a load device 5 that presses the indenter 4 to apply a testing force onto the test piece TP and a displacement sensor 6 that measures the displacement of the indenter 4. Also, in the frame 1, there is housed a plurality of objective lenses 7 attached to a revolving nosepiece. Observation light that enters into the objective lenses 7 is observed with an eyepiece unit 10 by an image formation optical system 8 and an eyepiece system 9. An imaging device not shown is disposed in the eyepiece unit 10. The observation image from the imaging device is input to a control device 20 through an A/D converter 11.

The displacement sensor 6 is constituted by, for instance, a differential transformer type displacement detector. The analog output of displacement sensor 6 is input from amplifier 12 to A/D converter 13, converted into the digital signal, and input to controller 20. The loading device 5 is constituted by, for instance, an adjustable load device of the electronic balance type. The load device 5 has an electromagnetic coil 51 to which electric current adjusted by a load current feeder 14 is supplied. The indenter 4 is pressed onto the test piece TP by the electromagnetic force of the electromagnetic coil 51 to apply a press load thereto. The press load is controlled by the supply current from the load current feeder 14. The control device 20 monitors a load current instruction value to the electromagnetic coil 51 to detect the press load by the indenter 4.

The control device 20 includes a CPU 21, a ROM 22, a RAM 23, an I/O 24, a touch panel monitor 25, and a recorder 26. The CPU 21 executes various processes to be detailed later according to a testing program stored in the ROM 22 as detailed later. A test condition setting screen, a test data display screen, and a test result display screen, and so on are displayed in the touch panel monitor 25. Moreover, various button switches to be detailed later are displayed in the touch panel monitor 25. The recorder 26 is connected with the I/O 24 to record the measurement data.

The CPU 21 relates the indentation depth detected by the displacement sensor 6 to the press load (testing force) applied to the test piece TP by the indenter 4 to prepare a testing force-indentation depth curve and obtains hardness therefrom. This process is an ordinary measurement process. Moreover, the CPU 21 executes a process to determine a filter constant in addition to the measurement process. That is, the CPU 21 analyzes the frequency characteristics of turbulence based on the output signal from the displacement sensor 6, and calculates a filter constant based on the analysis result. This process is called a filter constant calculation process. The CPU, 21 performs the filtering process defined by the filter constant to the displacement detection output from the displacement sensor 6 to remove the vibration component due to the turbulence. The filter constant is a parameter that defines the filter characteristics of a digital filter.

In the micro hardness meter of this embodiment, the hardness measurement test can be performed either according to a filter characteristics pre-measurement method in which a filter constant is calculated before the testing according to a displacement detection signal in a no-load state, or according to a filter characteristics post-measurement method in which a filter constant is calculated after the test is started according to a displacement detection signal in a loaded state.

According to the filter characteristics pre-measurement method, the filter constant is calculated by measuring the frequency component of the noise superimposed to the displacement detection signal measured in a no-load state before the test, and the data is sampled while performing the filtering process to the displacement detection signal to remove the noise. The entire data is sampled until the indenter 4 is indented to a predetermined indentation depth or until the indenting force reaches a predetermined value. The filtering process may be performed by using the filter constant calculated beforehand after all the displacement detection signals have been sampled.

According to the filter characteristics post-measurement method the displacement detection signals are sampled while pressing the indenter into the test piece, and the noise frequency superimposed to the displacement detection signal is analyzed to calculate a filter constant. Then the filtering process defined by the calculated filter constant is performed to the sampled displacement detection signal to remove the noise.

Figure 2:
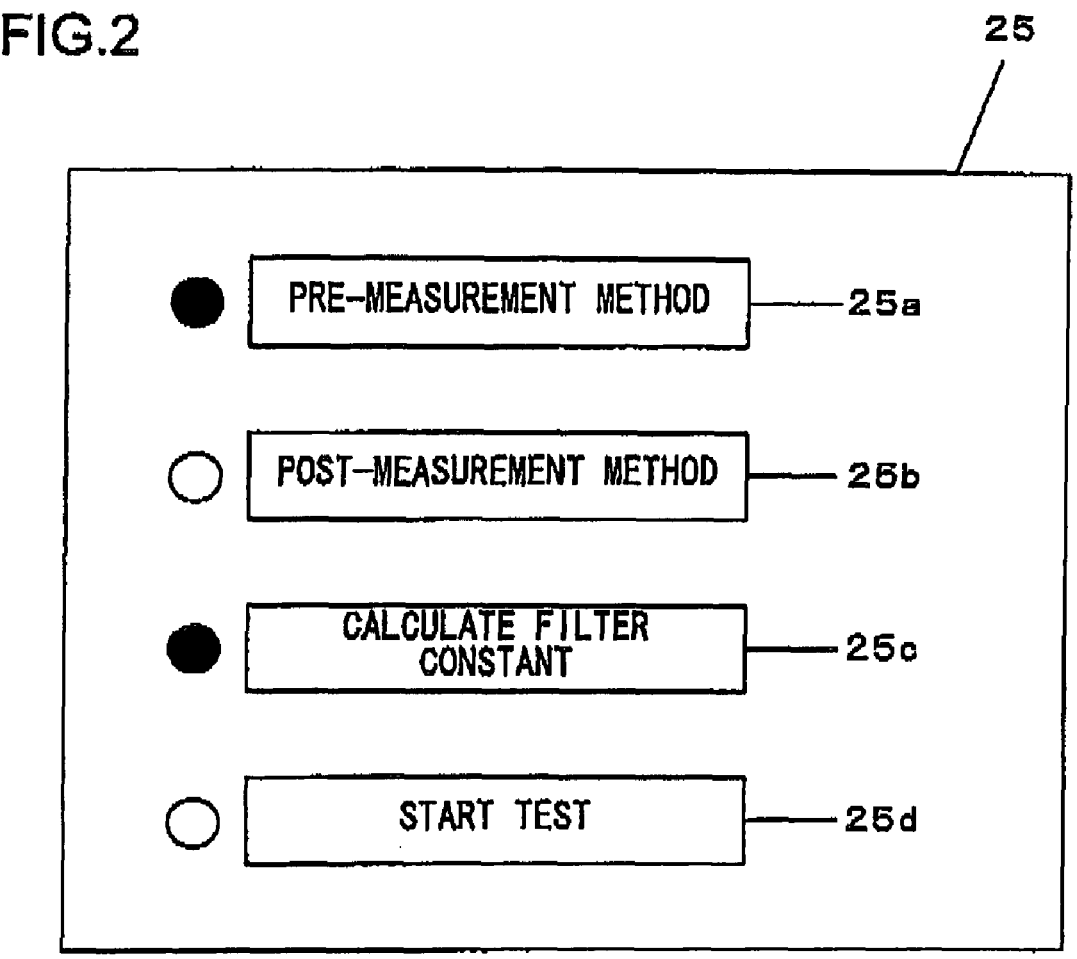
FIG. 2 is a diagram illustrating various buttons displayed on a monitor.

In the micro hardness meter of this embodiment as mentioned above, on the test condition setting screen of the touch panel monitor 25, a filter characteristics pre-measurement button 25a and a filter characteristics post-measurement button 25b are disposed as the mode selection buttons shown in FIG. 2 in order to enable selection of either one of the filter characteristics pre-measurement method and the filter characteristics post-measurement method. Moreover, when the filter characteristics pre-measurement method is selected, there are displayed a filter constant calculation button 25c to determine a filter constant and a test start button 25d to sample hardness measurement data. In the example of FIG. 2, there is indicated a case where the filter characteristics pre-measurement button 25a and the filter constant calculation button 25c have been operated.

—Filter Characteristics Pre-Measurement Method—

First of all, the testing procedure that adopts the filter characteristics pre-measurement method is described. The filter constant that is appropriate for a site where the micro hardness meter is set up is determined before testing by the following procedures 1-5.

When the filter characteristics pre-measurement method is selected with the filter characteristics pre-measurement button 25a, and the filter constant calculation button 25c is turned on, the following processing is started.

Procedure 1: The load current feeder 14 is controlled so as to hold the indenter 4 in a predetermined position in the air.

Procedure 2: The displacement detection signals from the displacement sensor 6 are sampled for a predetermined time and stored in the RAM 23.

Procedure 3: A string of the sampled displacement detection signal is read out from the RAM 23, and FFT analysis is performed thereon.

Procedure 4: The frequency characteristics of the noise are detected based on the FFT analysis result and a filter constant to remove the noise is calculated. The filter constant represents, for instance, a passing frequency of the low-pass filter and a threshold value of the band-pass filter.

Procedure 5: The filter constant is stored in the RAM 23.

Next, the hardness of the test piece TP is measured by the following procedures 11-15 by using the determined filter constant.

Procedure 11: The filter constant stored in the RAM 23 is read in by operating the test start button 25d.

Procedure 12: The indenter 4 is pressed onto the test piece TP at a predetermined displacement velocity to make an indentation. At this time, the displacement detection signal (indentation depth) and the load current instruction value (testing force) are sampled. These are related to each other and stored in the RAM 23. When the displacement detection signal is stored in the RAM 23, the read in filter constant is applied to the displacement detection signal to perform digital filtering process thereon to remove the noise. Moreover, a testing force-indentation depth curve is prepared based on the string of the displacement detection signals after the filtering process and the load current instruction value.

Procedure 13: The hardness of the test piece TP is evaluated based on the testing force-indentation depth curve.

Next, the testing procedure in which the filter characteristics post-measurement method is adopted is described.

Procedure 21: When the filter characteristics post-measurement method is selected with the filter characteristics post-measurement button 25b and the test start button 25d is operated, the indenter 4 is pressed onto the test piece TP at a predetermined displacement velocity to make an indentation. At this time, the displacement detection signals from the displacement sensor 6 are sampled, and at the same timing, an electric current instruction values that represent testing forces are sampled. The displacement detection signals (indentation depths) and the load current instruction values (testing forces) are sampled. These are related to each other and stored in the RAM 23.

Procedure 22: If a predetermined indentation depth is detected or a predetermined indenting force is detected, the indenting of the indenter 4 is ended.

Procedure 23: The string of displacement detection signal of the displacement sensor 6 is read out from the RAM 23, the FFT analysis is performed, the frequency band of the noise is detected, and the filter constant is determined.

Procedure 24: The determined filter constant is stored in the RAM 23 of the control device 20.

Procedure 25: The displacement detection signals and the filter constants of displacement sensor 6 are read out from the RAM 23, the digital filtering process is performed to the string of the displacement detection signals with the read in filter constant, and the displacement detection signals from which the influence of turbulence has been removed are stored to the RAM 23.

Procedure 26: The testing force corresponding to the displacement detection signal and the displacement detection signal from which the turbulence has been removed is read out, and a testing force-indentation depth curve is prepared.

Procedure 27: The hardness of the test piece TP is evaluated based on the testing force-indentation depth curve.

Figure 3:
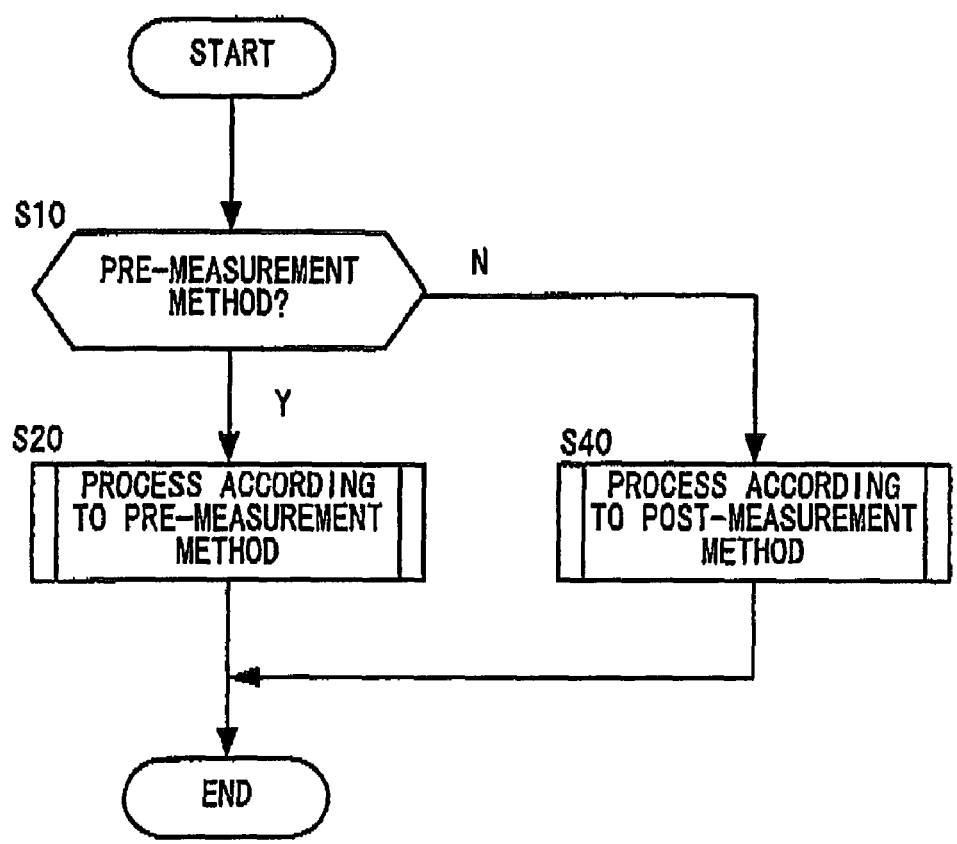

FIGS. 3-6 each are a flowchart of the program that causes the CPU 21 to execute the above-mentioned respective processes. The program of FIG. 3 is started up when the power supply of the micro, hardness meter is turned on. The control advances to the process according to filter characteristics pre-measurement method in step S20 when the filter characteristics pre-measurement method is selected with the filter characteristics pre-measurement button 25a in step S10. On the other hand, the control advances to the process according to the filter characteristics post-measurement method in step S30 when the filter characteristics post-measurement method is selected with the filter characteristics post-measurement button 25b in step S10.

Figure 4:
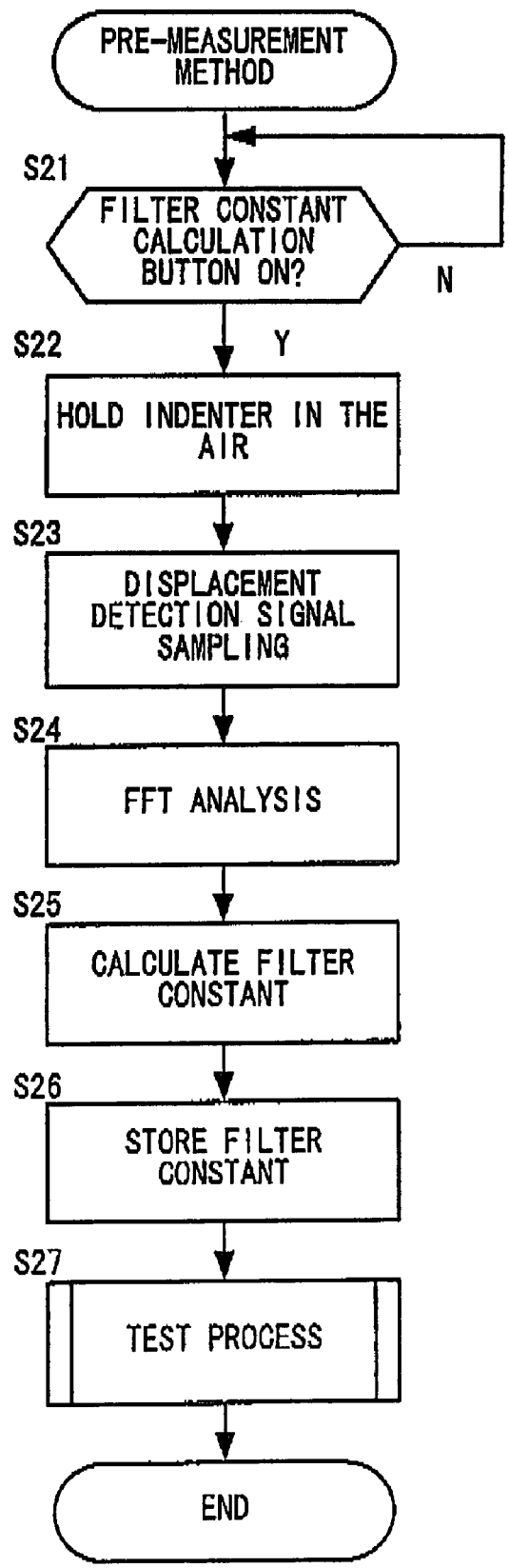
FIG. 4 is a flowchart that illustrates a filter constant calculation process according to a filter characteristics pre-measurement method.

FIG. 4 is a flowchart of the process according to the filter characteristics pre-measurement method. When the filter constant calculation button 25c is turned ON in step S21, the control proceeds to step S22 to control the load current feeder 14 to hold the indenter 4 at a predetermined position in the air. Then, in step S23, the displacement detection signals of the displacement sensor 6 are sampled for a predetermined time and the sampled signals are stored in the RAM 23. After a predetermined time has passed, the string of the sampled displacement detection signals is read out from the RAM 23, and FFT analysis is performed thereon in step S24. In step S25, the frequency band of the noise included in the string of the displacement detection signals is detected and the filter constant is calculated based on the result of the FFT analysis. The filter constant is stored in the RAM 23 in step S26. Thus, the filter constant is acquired beforehand and then the test processing is executed in step S27.

Figure 5:
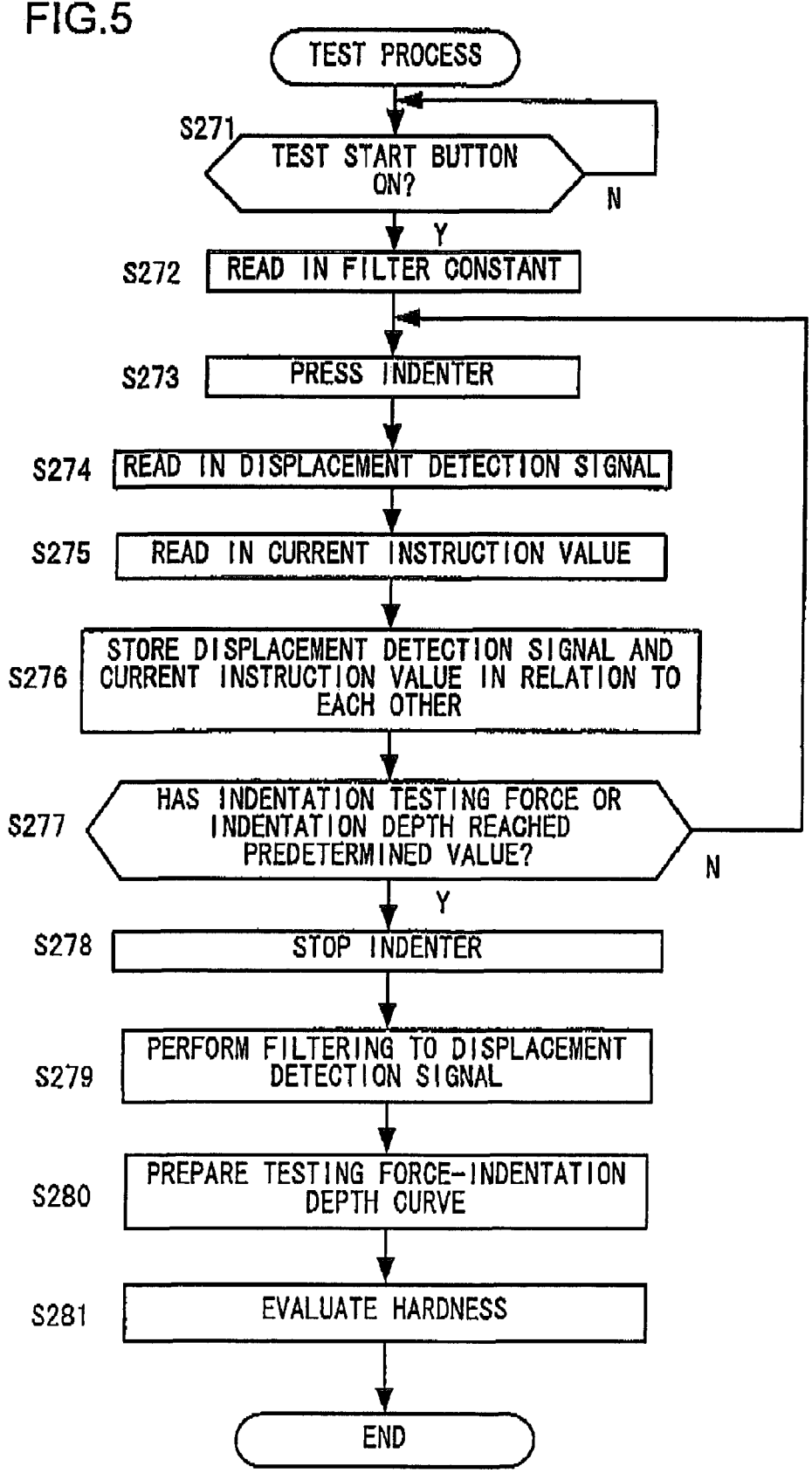
FIG. 5 is a flowchart following the one in FIG. 4, illustrating a test process according to a filter characteristics pre-measurement method.

FIG. 5 is a flowchart of the test process. When the test start button 25d is operated in step S271, the filter constant stored in the RAM 23 is read in during step S272. When the control is advanced to step S273, the indenter 4 is pressed onto the test piece TP at a predetermined displacement velocity to make an indentation. Steps S273-S277 is repeatedly executed while the indenter 4 is moving. That is, the displacement detection signals and the electric current instruction values are read in during steps S274 and S275, respectively, and the displacement detection signals and the electric current instruction values are mutually related and the related signals and values are stored in the RAM 23 in step S276.

When the indentation depth of the indenter 4 reaches a predetermined value, or when the indenting force reaches a predetermined value in step S277, the indenter 4 is stopped in step S278, and the control proceeds to step S279. In step S279, the digital filtering process is performed to the string of the displacement detection signals by using the filter constants read in during step S272. As a result, the noise superimposed to the displacement detection signal is removed. Moreover, in step S280, a testing force-indentation depth curve is prepared based on the string of the displacement detection signals and the load current instruction values after the filtering process. The testing force can be detected according to the electric current instruction value to the load current feeder 14 as mentioned above. The hardness of the test piece TP is evaluated based on the test force-indentation depth curve.

Next, the testing procedure in which the filter characteristics post-measurement method is adopted is described with reference to the flowchart of FIG. 6.

When the test start button 25*d* is operated in step S41, the indenter 4 is pressed onto the test piece TP at a predetermined displacement velocity to make an indentation in step S42. On this occasion, the displacement detection signals from the displacement sensor 6 and the load current instruction values representing the testing forces are sampled in steps S43 and S44, respectively. The displacement detection signals and the load current instruction values are related to each other and the related signals and values are stored in the RAM 23 in step S45. When it is determined in step S96 that the indentation depth by the indenter 4 has reached a predetermined value or that the indenting force has reached a predetermined value, the indenting of the indenter 4 is ended in step S47.

In step S48, the string of the displacement detection signals is read out from the RAM 23, and FFT analysis is performed. In step S49, the frequency band of the noise included in the string of the displacement detection signals is detected based on the result of the FFT analysis and a filter constant is calculated. The obtained filter constant is stored in the RAM 23. In step S50, the displacement detection signals and the filter constant of the displacement sensor 6 are read out from the RAM 23, and the digital filtering process with the filter constant is performed to the displacement detection signals. Moreover, in step S51, a testing force-indentation depth curve is prepared based on the string of the displacement detection signals and the load current instruction values after the filtering process. The testing force can be detected according to the electric current instruction value to the load current feeder 14 as mentioned above. In step S52, the hardness of the test piece TP is evaluated based on the test force-indentation depth curve.

According to the micro hardness meter described above, the noise can be removed by using the filter constant with which turbulence due to the vibration of the host site is appropriately removed even if the micro hardness meter is set up in various sites. Under the system requirements in which the host site is frequently changed and under an environment where the turbulence is changing momentarily, it is preferred that the filter constant is calculated according to the filter characteristics post-measurement method each time. Under the system requirements in which the host site is not frequently changed, without changes of the turbulence, it is preferred to select the filter characteristics pre-measurement method and to calculate the filter constant before the testing in order to shorten the testing time.

In particular, the present invention is suitable for an indenting type material testing machine that uses a minute testing force as in physical properties evaluation tests for thin films and as a result enables evaluation of materials under a testing condition that the indentation depth of one micrometer (1 μm) or less.

According to the filter characteristics post-measurement method described above, the filter constant is determined according to the string of the displacement detection signals that have been sampled while the indenter is being pressed onto a predetermined depth. That is, after the entire test data has been sampled, FFT analysis is performed on the string of the displacement detection signals. However, the FFT analysis may be performed to the string of the displacement detection signals sampled for a predetermined time in an early stage from the start of the indenting to calculate a filter constant, and the filtering process may be performed to the subsequent sampled data in real time. The frequency component of the noise may be detected by the techniques other than the FFT analysis.

As mentioned above, any one of the filter characteristics pre-measurement method and the filter characteristics post-measurement method is selected before the testing. However, the indenting type material testing machine may be adapted such that it adopts only either one of them.

Moreover, the filtering process to the displacement detection signals is by digital processing in the CPU. However, an analog type device such as a low-pass filter or a band-pass filter that removes the noise component may also be used. The filter characteristics in this case should be adapted to be changeable according to an instruction from the CPU.

The micro hardness meter has been described above. However, the present invention is not limited to the micro hardness meter mentioned above as far as the material testing machine of the present invention enables testing for the evaluation of the physical properties of materials by pressing the indenter onto a test piece and by using at least displacement detection signals. For instance, the present invention can be applied also to a testing machine that measures modulus of elasticity etc. from an unloading curve.

According to the present invention, existing material testing machines can be provided with a function to calculate filter constants and a function to perform a programmable filtering process by rewriting the testing program implemented in the existing material testing machine. That is, the testing program product for testing in accordance with the present invention is to cause a computer to execute: pressing an indenter onto a test piece; detecting displacement of the indenter; detecting a testing force applied to the test piece by the indenter; performing an FFT analysis to the detected displacement detection signal to detect a frequency band of a noise; calculating filter characteristics based on the detected frequency band; filtering the displacement detection signal based on the calculated filter characteristics; and evaluating physical properties of the test piece based on the displacement detection signal after the filtering and a testing force.

Moreover, the present invention can be realized as a material testing machine that includes: a measurement device that measures frequency characteristics of turbulence noise superimposed to the detection signal; an arithmetic device that analyzes the frequency characteristics to determine the filter constant; a filtering device that performs filtering defined by the filter constant to the detection signal; and an evaluation device that evaluates the material by using the detection signal to which the filtering is performed by the filtering device.

In addition, the present invention is not limited to the above-mentioned embodiments as long as the feature of the present invention is not damaged.

The invention claimed is:

1. An indenting type material testing machine comprising:
   an indenter for pressing a test piece;
   a load device that applies a load to the test piece through the indenter;
   a displacement sensor that measures displacement of the indenter;
   a calculation device that calculates filter characteristics that remove a turbulence component in a displacement detection signal based on the displacement detection signal obtained from the displacement sensor in a no-load state;
   a storage unit that stores the filter characteristics calculated by the calculation device; and
   a filtering device that performs filtering to the displacement detection signal based on the filter characteristics stored in the storage device.

2. An indenting type material testing machine according to claim 1, further comprising:
   a selection member that selects any one of a preparation mode in which the displacement signal is sampled to calculate the filter characteristics and a test mode in which the displacement detection signal is sampled to calculate material evaluation data, wherein
   when the preparation mode is selected, the displacement detection signal is sampled, with the indenter being held in a position in a no-load state.

3. An indenting type material testing machine comprising:
   an indenter pressed onto a test piece;
   a load device that applies a load to the test piece through the indenter;
   a displacement sensor that measures displacement of the indenter;
   a calculation device that calculates filter characteristics that remove a turbulence component in a displacement detection signal based on the displacement detection signal obtained from the displacement sensor in a loaded state;
   a storage unit that stores the filter characteristics calculated by the calculation device; and
   a filtering device that performs filtering to the displacement detection signal based on the filter characteristics stored in the storage device.

4. A material testing machine according to claim 3, wherein
   the calculation device calculates the filter characteristics based on the displacement detection signal sampled in an initial stage of starting pressing of the indenter; and
   the filtering device performs the filtering process to the displacement detection signal output thereafter according to the filter characteristics.

5. An indenting type material testing machine according to claim 1, further comprising:
   an arithmetic device that calculates an indentation depth of the indenter-testing force curve based on the detection signal from the displacement sensor having subjected to the filtering process by the filtering device and an indenting force of the indenter by the load device to calculate the hardness of the test piece.

6. A testing method comprising:
   pressing an indenter onto a test piece;
   detecting displacement of the indenter;
   detecting a testing force applied to the test piece by the indenter;
   detecting a frequency band of noise in a detected displacement detection signal of the indenter;
   calculating filter characteristics based on the detected frequency band;
   filtering the displacement detection signal based on the calculated filter characteristics; and
   evaluating physical properties of the test piece based on the displacement detection signal after the filtering and the detected testing force.

7. A testing method according to claim 6, wherein
   the displacement detection signal when the frequency band of the noise is detected is a signal sampled in a no-load state in which the indenter is not in contact with the test piece.

8. A testing method according to claim 6, wherein
   the displacement detection signal when the frequency band of the noise is detected is a signal sampled in a loaded state in which the indenter presses the test piece.

9. A non-transitory computer-readable medium storing instructions for causing a computer to execute a method of testing, the method comprising:
   pressing an indenter onto a test piece;
   detecting displacement of the indenter;
   detecting a testing force applied to the test piece by the indenter;
   detecting frequency band of a noise in a detected displacement detection signal of the indenter;
   calculating filter characteristics based on the detected frequency band;
   filtering the displacement detected signal with the calculated filter characteristics; and
   evaluating physical properties of the test piece based on the displacement detection signal after the filtering and the detected testing force.

* * * * *